(12) United States Patent
Hayes-Gill et al.

(10) Patent No.: US 11,089,992 B2
(45) Date of Patent: Aug. 17, 2021

(54) FETAL MOVEMENT MONITOR

(71) Applicant: Monica Healthcare Limited, Nottingham (GB)

(72) Inventors: Barrie Hayes-Gill, Nottingham (GB); Jean Francois Pieri, Nottingham (GB)

(73) Assignee: Monica Healthcare Limited, Nottingham (GB)

( * ) Notice: Subject to any disclaimer, the term of this patent is extended or adjusted under 35 U.S.C. 154(b) by 716 days.

(21) Appl. No.: 14/781,629

(22) PCT Filed: Apr. 2, 2014

(86) PCT No.: PCT/GB2014/051037
§ 371 (c)(1),
(2) Date: Oct. 1, 2015

(87) PCT Pub. No.: WO2014/162135
PCT Pub. Date: Oct. 9, 2014

(65) Prior Publication Data
US 2016/0058363 A1    Mar. 3, 2016

(30) Foreign Application Priority Data
Apr. 2, 2013  (GB) ...................................... 1305937

(51) Int. Cl.
*A61B 5/00*    (2006.01)
*A61B 5/11*    (2006.01)
(52) U.S. Cl.
CPC .......... *A61B 5/4362* (2013.01); *A61B 5/0011* (2013.01); *A61B 5/11* (2013.01);
(Continued)
(58) Field of Classification Search
CPC ............................ A61B 5/4362; A61B 5/0011
See application file for complete search history.

(56) References Cited

U.S. PATENT DOCUMENTS 5,817,035 A    10/1998 Sullivan
2009/0270767 A1    10/2009 Nishihara et al.
(Continued)

FOREIGN PATENT DOCUMENTS

EP    1220640    7/2002
EP    1680018    7/2009
(Continued)

OTHER PUBLICATIONS

Sadovsky et al., The Incidence of Different Types of Fetal Movements During Pregnancy, British Journal of Obstetrics and Gynaecology, Jan. 1, 1979, pp. 10-14, vol. 86, No. 1.
(Continued)

*Primary Examiner* — Daniel L Cerioni
*Assistant Examiner* — Yasmeen S Warsi (57) ABSTRACT

The invention concerns fetal movement monitoring apparatus having a deflection sensor device arranged to be applied to a mother's abdomen for detection of abdominal deflections indicative of fetal movements and to output a signal comprising one or more record of said abdominal deflections. A processor under the control of machine readable instructions is arranged to process the signal output from the deflection sensor device and to output a log of fetal movement over time. The processor is arranged to receive one or more further input indicative of maternal or fetal movement or wellbeing, for example from a second sensor device by which a user can input a record of perceived fetal movements. The processor may compare the output of the first sensor device and the user's input via the second sensor device and output a log of fetal movements over time based upon said comparison.

23 Claims, 4 Drawing Sheets

(52) U.S. Cl.
CPC ........... *A61B 5/1116* (2013.01); *A61B 5/1118* (2013.01); *A61B 5/6804* (2013.01); *A61B 5/6833* (2013.01); *A61B 5/725* (2013.01); *A61B 5/7246* (2013.01); *A61B 5/7282* (2013.01); *A61B 5/742* (2013.01); *A61B 5/746* (2013.01); *A61B 5/7475* (2013.01); *A61B 2503/02* (2013.01); *A61B 2505/07* (2013.01); *A61B 2560/0475* (2013.01); *A61B 2562/0219* (2013.01); *A61B 2562/164* (2013.01)

(56) References Cited

U.S. PATENT DOCUMENTS

| | | | |
|---|---|---|---|
| 2010/0191154 A1* | 7/2010 | Berger | A61B 5/02411 600/595 |
| 2011/0306893 A1 | 12/2011 | Harrold | |
| 2012/0150010 A1* | 6/2012 | Hayes-Gill | A61B 5/02411 600/382 |
| 2012/0232398 A1* | 9/2012 | Roham | A61B 8/0866 600/453 |
| 2012/0302854 A1* | 11/2012 | Kamath | A61B 5/14532 600/365 |

FOREIGN PATENT DOCUMENTS

| | | |
|---|---|---|
| EP | 2328471 | 6/2011 |
| GB | 2471667 A | 1/2011 |
| WO | 0126545 A1 | 4/2001 |
| WO | 2004012598 A2 | 2/2004 |
| WO | 2005039410 A1 | 5/2005 |
| WO | 2008010216 A2 | 1/2008 |
| WO | 2009150440 A1 | 12/2009 |

OTHER PUBLICATIONS

International Search Report, International Application No. PCT/GB2014/051037, dated Jun. 3, 2014.

Luterkort et al., Fetal motor activity in breech presentation, Early Human Development, Jan. 1, 1985, pp. 193-200, Elsevier Science Publishers B.V. (Biomedical Division).

Sadovsky et al., Correlation Between Electromagnetic Recording and Maternal Assessment of Fetal Movement, The Lancet, May 26, 1973, pp. 1141-1143, vol. 301, No. 7813.

William F. Rayburn, MD, Monitoring Fetal Body Movement, Clinical Obstetrics and Gynecology, Dec. 1987, 13 pages, vol. 3, No. 4.

Eiji Ryo, et al., A new method for long-term home monitoring of fetal movement by pregnant women themselves, Medical Engineering and Physics, Sep. 4, 2011, 7 pages, Elsevier Ltd.

Written Opinion of the International Searching Authority, PCT/IB/373, dated Oct. 6, 2015, 5 pages, WIPO, Switzerland.

\* cited by examiner

FETAL MOVEMENT MONITOR

This invention concerns the monitoring of fetal movements, commonly referred to as fetal activity, in the womb.

Fetal body movements in utero, as distinct from other vital signs, such as a fetal heartbeat, are known to provide an indication of fetal wellbeing. Studies have shown correlations between fetal health and fetal movements, wherein a healthy fetus will typically move or kick to a greater extent than an unhealthy fetus. Pregnancies affected by decreased fetal movement bear an increased risk of adverse outcome leading to fetal death as reported, for example by Mangesi L, Hofmeyr G J, "Fetal movement counting for assessment of fetal wellbeing" (*Cochrane Database of Systematic Reviews*. 2007. p. CD004909).

Whilst it is possible for fetal movement to occur in response to external stimuli, it is generally accepted that there exists a baseline of fetal movement which occurs as a part of the physiological development of the fetus, aside from such externally stimulated movement. For this reason, expectant mothers are commonly advised to count the number of fetal kicks experienced within a predetermined period of time. Several counting protocols have been applied in an attempt to quantify these movements. In one technique the mother is asked to lie on her side and count distinct fetal movements. Here the mother is asked to record the time it takes to record more than 10 fetal movements. The perception of 10 or more fetal movements by the mother typically occurs within 60 minutes and is classified as a reassuring sign of fetal wellbeing.

Alternatively, the mother counts fetal movement for one hour, three times a week. A reassuring count is considered to be one which equals or exceeds the previous count. Such counting procedures are inconvenient for the mother and extremely subjective, especially if little guidance is provided by a clinician. Perhaps more commonly, a mother will have a general feel for how many kicks they have experienced within a day and will only stop to actually count fetal movements if they are concerned that they have experienced fewer than normal fetal movements.

However the fetal movement sensations experienced by different mothers may vary based on a number of factors, including a mother's build, general activity levels, whether or not this is their first pregnancy, etc. During periods of relatively high maternal activity, the number of fetal movements may be reduced or else movements may go unnoticed by the mother. Conversely, fetal activity can be artificially increased for certain periods of time, for example after eating or drinking.

Accordingly maternal "self-screening" techniques for monitoring fetal activity are often unreliable and so further, less-subjective monitoring techniques have been developed for use by midwives and clinicians.

Doppler ultrasound techniques require that a signal of a suitable frequency is directed at the fetus using a crystal transducer applied to the mother's abdomen. The signal reflected from the fetus is shifted by a small frequency which is caused by movements of various parts of the fetus. Normally ultrasound is employed to identify pulsations of the fetal heart in order that a fetal heart rate can be produced as part of a cardiotocograph (CTG). To detect fetal heart movements the Doppler ultrasound processed signal is narrow band filtered to select the fetal heart movements and hence fetal heart rate. However by exploring a wider bandwidth other types of fetal movements can be detected, such as fetal chest wall movements, i.e. to provide an indication of fetal breathing.

This technique is often referred to as an Actogram. A limitation of the Actogram technique is that careful positioning of the Doppler transducer is required and so a skilled clinician or midwife must locate the transducer on the abdomen and reposition the transducer whenever the fetus moves.

An alternative technique is the ultrasound imaging technique that looks at the transit time of pulsed ultrasound signals and enables images of organs and structures within the human body to be displayed on a monitor. Ultrasound imaging enables specific movements to be identified and quantified. However the equipment size and cost limits its applicability such that it is only used for detailed assessments within a hospital or other medical facilities. Furthermore prolonged exposure to ultrasound can pose risks for the fetus. Accordingly such advanced techniques are used infrequently, such as at one or two prescribed appointments during a pregnancy or else in response to circumstances giving rise to concern over maternal or fetal wellbeing.

In view of the above, there is scope for improved monitoring of fetal movements without requiring the fetus and/or mother to attend a medical facility for assessment.

It may be considered an aim of the invention to provide equipment offering more reliable and/or convenient monitoring of fetal activity in a home environment.

According to a first aspect of the present invention there is provided fetal movement monitoring apparatus comprising a deflection sensor device arranged to be applied to a mother's abdomen for detection of abdominal deflections indicative of fetal movements and to output a signal comprising one or more record of said abdominal deflections; and one or more processor under the control of machine readable instructions arranged to process the signal output from the deflection sensor device and to output a log of fetal movement over time.

The processor may be arranged to receive one or more further inputs indicative of maternal or fetal movement or wellbeing and to compare said further input with the signal output from the deflection sensor. The output log of fetal movement may be based upon said comparison. The further input may comprise one or more record of sensed, predicted, measured or perceived fetal or maternal movement. The further input may be in respect of a corresponding time period as the record output by the sensor device.

The monitoring apparatus may comprise a user interface device. A user may use the device to input a record of perceived fetal movements. The user may be a mother or another person, such as a medical professional or other carer, who can input a log of fetal movement based on one or more perceived phenomena (e.g. visible, audible or tactile phenomena).

The user interface device may comprise the one or more processors. The user interface device may comprise a receiver or transceiver. The user interface device may be in wired or wireless communication with the deflection sensor device. In an additional embodiment, the one or more processors may comprise a separate computing device which is arranged to receive both an output of the user interface device and the signal output from the deflection sensor device via wired or wireless communication means.

The user interface device may comprise a remote device with respect to the deflection sensor device.

The user interface device may be a portable device such as a portable electronics and/or communication device. The device may be a portable telephone, laptop, PDA, tablet computer or other computing device. Alternatively, the user interface device may comprise a personal computer. The user interface may comprise a touch sensitive interface, for example having one or more keys or buttons or a touch-sensitive screen.

The deflection sensor device may be considered to comprise a first sensor device. The remote device may be considered to comprise a second sensor device, wherein, for example, the user interface comprises a tactile sensor.

The deflection sensor device may comprise one or more deflection sensor and a bandpass filter. The deflection sensor may comprise a stress or strain sensor. The deflection sensor may comprise a piezo-electric member.

The deflection sensor device may comprise a transmitter, such as for example a wireless radio transmitter.

The deflection sensor device may comprise a power source.

The deflection sensor device may comprise two or more deflection sensors for application at spaced locations or different orientations on the mother's abdomen. The deflection sensors may be arranged at different angles, such as for example at right angles. The deflection sensors may be elongate in form and may display greatest sensitivity in a longitudinal direction, rather than a lateral direction.

The deflection sensor device may comprise a patch, pad or garment arranged to be worn by a mother.

Embodiments of the invention advantageously offer the ability to allow unobtrusive and/or wireless monitoring of fetal movement by a mother or carer in a natural home setting. This allows monitoring to be undertaken for prolonged periods of time such as over one or more days, weeks or months or even over one or more trimesters. This can provide a useful source of additional data and/or monitoring facilities available to the obstetrician and the clinical community to supplement the existing, conventional monitoring technologies.

In one embodiment, the apparatus may comprise a further sensor or sensor device. The further sensor may comprise a maternal movement sensor. The further sensor may be arranged to be applied to the mother's skin, or worn by the mother, for example on or in the vicinity of the mother's abdomen. The further sensor may be comprised within the deflection sensor device or may be a separate sensor device. The further sensor may comprise an accelerometer.

The further sensor may output a signal indicative of movements of the mother, for example comprising one or more records of movement. The one or more processor may be arranged to receive the signal output from the further sensor. The processor may be arranged to compare signal output from the further sensor with the input via the user interface and/or the signal output from the deflection sensor device (or the comparison thereof) and to output the log of fetal movements over time based upon said comparison.

The processor may discount or remove a sensed fetal movement record where it occurs during a period of maternal movement. The processor may discount or remove a sensed fetal movement record if a concurrent maternal movement of above a predetermined threshold variable value is determined, for example if the magnitude of the sensed maternal movement is above a threshold value.

The records of fetal and/or maternal movement may comprise any or any combination of time, duration, magnitude of movement in one or more directions, peak magnitude and/or direction of movement.

The comparison by the processor may comprise comparing the time and/or duration of any records or signals. The comparison may comprise comparing any of the parameters defined herein in relation to the records of fetal and/or maternal movement.

The processor may determine an instance of fetal movement where the time of sensed fetal movement coincides with a time of input of a perceived fetal movement by the mother or other user. The processor may apply a predetermined time/duration threshold for said comparison, which may comprise a few seconds.

For example a user's input may be determined to coincide with a sensed fetal movement if it occurs within 10 seconds or less of the sensed movement.

The log of fetal movements may comprise a fetal movement count over a predetermined time period and/or a log of the timings of a plurality of fetal movements. The log may comprise any other fetal movement parameter referred to herein.

The log of fetal movements may be transmitted to a medical facility.

The processor may determine the log of fetal movements at predetermined time intervals. The sensor(s) and/or input device may be arranged to store inputs/records for later access to the processor. The processor may compare the log of fetal movements to one or more predetermined threshold values, such as a predetermined count or rate of fetal movement and may output an alarm or a signal indicative of abnormal or reduced fetal movement if the log of fetal movement is below or outside of said predetermined threshold values.

The threshold value(s) of fetal movement may be static or may change over time according to, for example, a predetermined trend or else in response to previous logs of fetal movement. In one example, the threshold value(s) may change according to predetermined diurnal variations in normal fetal activity during gestation. In one embodiment, the processor may compare the output of the deflection sensor device with a record of such predetermined variations in normal fetal activity in addition to, or instead of, the input of perceived fetal movement.

The processor may determine a confidence level or value associated with any, or any combination, of: the mother's/user's input via the user interface; the output of the comparison by the processor; and/or the signal output from the deflection sensor device. Accordingly the processor may have a learning mode in which it compares the user's input via the user interface and with the signal output from the deflection sensor device. The confidence level parameter determined from the learning mode may be applied during a second mode of operation, for example a normal mode of operation, in which the processor may analyse/process or receive only one of the user's input via the user interface or the signal output from the deflection sensor device. The processor may output the log of fetal movements based on the received records/signals and said confidence value. Additionally or alternatively, the processor may output said confidence value with the log of fetal movement.

The learning mode and/or confidence value indicator advantageously allows the sensor device to continue operation without active input by the mother or another user. The confidence value may also provide useful information to medical personnel reviewing the mother's records at a later date since it may allow some interpretation of a fetal movement log.

The processor may interrogate the log or a plurality of logs representing an extended period of time, in order to identify one or more features or trends in fetal activity. For example, a feature may comprise a sudden change in gradient of a plot of fetal activity or else a period of uncharacteristic activity, e.g. sporadic activity or non-activity. The processor may change a confidence level or output a signal in response to determination of any such feature.

In any embodiment, if a feature is determined as being indicative of abnormal fetal activity, the processor may control output of an instruction via the user interface to the mother to undertake a learning/calibration mode of operation of the apparatus.

According to a second aspect of the invention there is provided a system comprising the apparatus of the first aspect and a remote computer or server at a medical facility, the processor device of the apparatus being arranged to transmit the log of fetal activity to said computer or server, such that the log is accessible within the medical facility.

The transmission may be via conventional wired or wireless communication, for example over one or more wide area networks, for example comprising a mobile telephony network and/or the internet.

The medical facility may comprise a data store, on which a log of fetal activity for the mother may be maintained, for example as a part of the medical records for the mother. The stored data may comprise a plurality of logs transmitted over a period of time by the processor device.

According to a third aspect of the invention, there is provided a method of monitoring fetal movement using the apparatus or system of the first or second aspects.

According to a fourth aspect of the invention there is provided a data carrier comprising machine readable instructions for the operation of one or more processor to process the signal output from the deflection sensor device and to output a log of fetal movement over time.

The machine readable instructions may comprise software or an 'app' to be loaded on a user interface device.

Any of the preferable features defined in relation to the first aspect may be applied to the second or third aspects.

Practicable embodiments of the invention are described in further detail below by way of example only with reference to the accompanying drawings, of which.

The invention maybe considered to derive from the premise that a fetal movement sensor, for example which is portable and/or can be applied to a mother's abdomen for extended periods of time, can be combined with one or more other types of sensor output or other fetal activity results in order to provide a sensing system suitable for home use by a pregnant mother.

Figure 1:
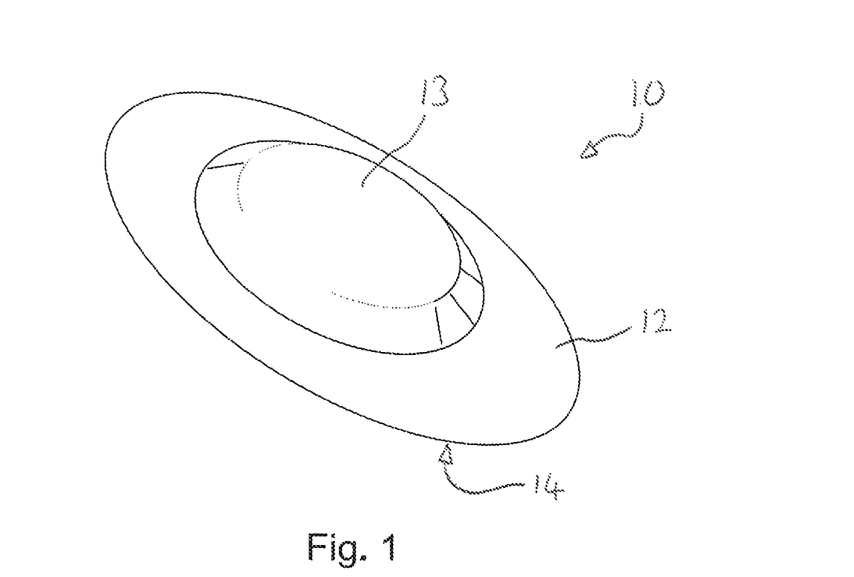
FIG. 1 shows a three-dimensional view of a sensor device for use within a system according to one example of the invention.

Turning firstly to FIG. 1 there is shown an example of a sensor device 10 which can be applied to a mother's abdomen for sensing/recording fetal movement. The device comprises a patch or pad portion 12 and a housing 13 for enclosing electronic circuitry and/or components associated with the fetal movement sensor. In this embodiment, the patch 12 comprises a biocompatible adhesive material on its underside 14, which may comprise an adhesive layer. The underside of the patch 12 may comprise for example an aqueous polymer material or layer, such as a gel. The patch may comprise a hydrogel material. Any conventional gel or adhesive material capable of maintaining the patch against the wearer's skin for extended periods of time, such as one or more days may be used. Ideally the patch is capable of removal and reapplication once or a small number of times such that each patch could be used for up to, or greater than, one week.

The patch 12 is used to locate a sensor in close proximity to the mother's abdomen. In this example the sensor comprises one or more deflection sensors 16. When the fetus moves the abdomen can often be seen to change shape and a measure of abdominal deflection can therefore provides a measure of fetal movements. There are several transducers that can possibly be used to detect these small deflections on the abdomen. However the choice of a suitable sensor requires careful consideration of both the sensitivity and bandwidth.

In this embodiment a piezo electric material made for example from Polyvinylidene fluoride (PVDF) is selected. A rectangular element of piezoelectric film is provided with a metallic layer on one or more sides thereof. In this embodiment a silver layer is provided using a silver-containing ink that may be provided on both sides of the piezoelectric film, for example by screen printing. One such device of this kind is the FLDT1-028K supplied by Measurement Specialties Ltd.

A biocompatible adhesive is provided on one side of the sensor either independently, or in this embodiment in conjunction with the patch adhesive described above, such that the sensor element is held within the patch by the adhesive layer.

Figure 2:
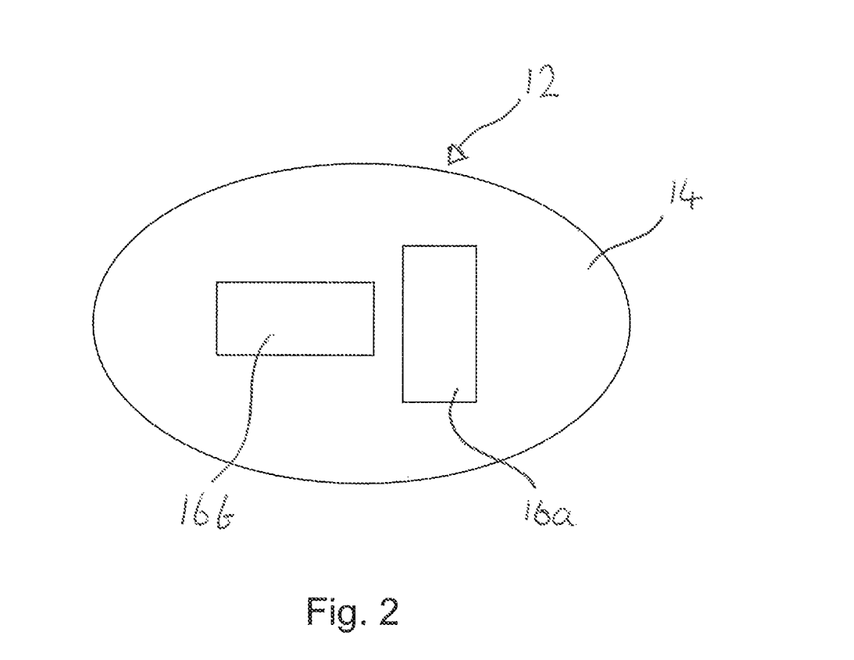
FIG. 2 shows a plan view of the sensor arrangement in FIG. 1.

As shown in FIG. 2, two such elongate piezoelectric sensors 16a and 16b are provided on the underside of the patch. The two sensors lie in substantially the same plane. The first sensor 16a is arranged such that it extends in a substantially orthogonal direction with respect to the second sensor 16b. The first and second sensors may be spaced apart or could be integrated into a single member which could for example be X-shaped or T-shaped in plan. PVDF sensors are typically more sensitive in the longitudinal direction than the transverse direction and so the sensor device 10 deploys two sensors mounted at an angle to each other on the abdomen in order to increase the effectiveness of the device.

Figure 4:
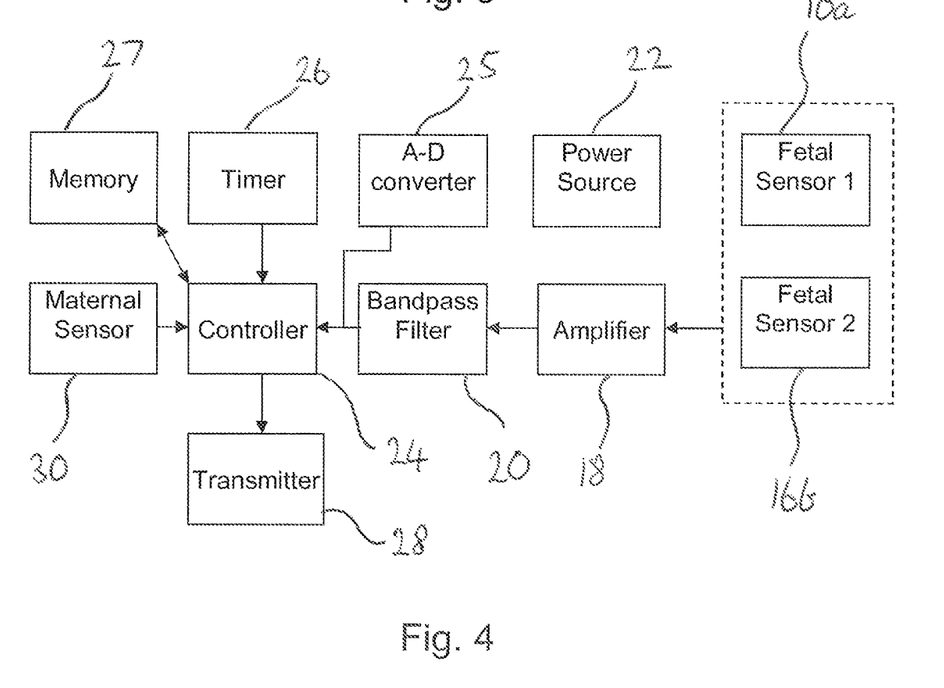
FIG. 4 shows a schematic arrangement of the electronic components according to one example of the invention.

Turning now to FIG. 4, there is shown a schematic of the electronics within the housing 13 of the sensor device. In some embodiments the housing 13 comprises a rigid cover, typically formed of a plastic material and having a hollow or concave interior in which the electronic components can be housed. The housing may comprise a dome or "button".

In one preferred embodiment the housing, including its internal components is detachable from the patch portion 12 such that the housing is reusable, whereas the patch may be disposable. Thus the housing 13 may be reattached to a further patch such that a single housing 13 can be used for the duration of one or more pregnancies. It may be advantageous to have a single housing for each mother such that data obtained from the sensor device 10 may be readily assignable to that mother.

The housing may be removably adhered to the patch. The patch may comprise one or more electrical connectors for attachment to corresponding connector(s) on the housing. Additionally or alternatively, the patch and/or housing may have one or more attachment formation, such as a slot, groove, clip or similar retaining formation for locating the housing on the patch.

The electrical components of the device comprise amplifier 18, a signal filter 20, a power source 22, a controller 24, a timer 26, which may be comprised with the controller 24, and a signal transmitter 28. The electrical components within the housing 13 as described below and/or as shown in FIG. 4 may collectively be considered to comprise a monitoring unit.

The output from the sensor(s) 16a, 16b is a small current proportional to the amount of deflection of the piezoelectric material caused by deflection of the mother's skin in the abdomen. This current is fed into a charge/signal amplifier 18 and the output from this amplifier is a voltage proportional to the magnitude of the deflection.

The output signal from the amplifier 18 passes to filter 20, which may comprise a low-pass, high-pass or bandpass filter dependent on the type of sensors used. The signal is typically $2^{nd}$ or $3^{rd}$ (or higher) order bandpass filtered. The signal filtering removes phenomena detected by the sensors having a frequency which is uncharacteristic of fetal movements. In the present example, the signal may be bandpass filtered for example between 0.1 and 150 Hz or else from 0.2 Hz to 120 Hz or else a narrower band within this frequency range.

An analogue-to-digital converter 25 digitizes the analogue sensor signals such that the resulting discrete data entries can be processed by a controller 24. The analogue-to-digital converter preferably samples the analogue input at greater than 100 or 200 Hz, for example at approximately 300 Hz or more.

The controller 24 may comprise one or more programmable microchip under the control of one or more modules of machine readable code. The controller receives the output of the filter 20 and processes the signal for transmission and/or local storage on memory device 28. For example, in one embodiment the controller may simply format the received data for storage or transmission. In such an embodiment, a further processor, to be described herein, would process the received data and perform further analysis thereof.

However in the present embodiment it is preferred that the local processor 24 in the sensor device 10 performs at least a first stage of data processing. This may help reduce the volume of transmitted/stored data and may output data in a more readily useable and understandable format. In such an embodiment, the processor 24 may process the magnitude and/or timing or duration of the sensed disturbances. The processor may assess the sensed disturbances against predetermined threshold criteria. In the event that the magnitude and/or duration of a sensed deflection meets or exceeds a threshold criterion, an instance of fetal movement may be logged. The record of fetal movement may comprise any, or any combination of, a time, duration, magnitude and/or direction of the disturbance. The record including such parameter value(s) may be stored in the local memory 27 for subsequent transmission to an external device as will be described below.

In the event that two or more deflection sensors are provided, the controller may compare the data signals from each sensor and may record or reject features in the received data as instances of fetal movement based on said comparison. For example, if two sensors each record, within a predetermined time threshold, a corresponding deflection, the controller may record a fetal movement in relation thereto, even if the magnitude of those deflections is relatively low. If only one sensor records a deflection (e.g. at or above the predetermined minimum threshold value), whereas the other does not, then the controller may require a relatively large magnitude of deflection in the single sensor reading before a log of fetal movement is output. Thus the use of two or more deflection sensors can increase the confidence of fetal movement recordal.

Also shown in FIG. 4 is a maternal movement sensor 30. The maternal movement sensor 30 provides a further sensor signal input to the controller 24. In this embodiment the maternal movement sensor is housed/mounted within the sensor device 10. However it is possible in other embodiments that the maternal movement sensor may be positioned remotely of device 10 and connected thereto by a wired or wireless connection. The maternal movement sensor may be incorporated into one or more abdominal electrodes, or it could be separately attached to the maternal body in order to allow for optimal positioning.

The maternal movement sensor comprises one or more sensors capable of detecting coarser or gross movement by the mother as opposed to the isolated abdominal deflections caused by fetal movements. In one example, the maternal movement sensor comprises an accelerometer. However any device capable of providing an indication of physical movement, or acceleration, of the maternal body or abdomen may be used. Various activity instruments, sensors, or transducers are possible, such as a gyro, an inertial motion sensor; mercury switches, smart materials on the abdomen (i.e. those whose resistance for example changes with movement), etc. A 1D, 2D or 3D movement sensor, e.g. accelerometer may be used.

In a preferred embodiment, the movement sensor is a 3D accelerometer having three independent sensors each capable of detecting motion or movement in one of the three Cartesian coordinate axes. Each sensor may have a full scale sensitivity of 2 g (where "g" refers to the acceleration determined by earth's gravity). The instantaneous acceleration measure for each of the three axes' sensors can be combined (for example by summation of absolute acceleration values in each direction) to form a combined or total activity measure, which may thus be non-directional.

In producing a quantification/measure of maternal movement, the current accelerometer values (e.g. in each direction) may be subtracted from the previous values. This can provide a high pass filter which can remove acceleration due to gravity and flicker (1/frequency) noise.

Any, or any combination, of signal amplification, filtering and/or analogue-digital conversion may be undertaken prior to receiving or recording of instantaneous maternal movement values by the processor 24. The sensor readings may be sampled at an equal, similar or lower rate than that of the fetal movement sensors. In one embodiment the activity measure may be summed or integrated over time to provide an indication of maternal movement or activity over a time period or window. An average of movement over that window may be recorded. The time windows may be for example a small number of seconds of between 1 and 10 seconds. Sampling may take place at between for example 1 and 100 Hz, such as for example between 10 and 50 Hz.

The value of the average maternal movement or activity for each time window is represented as a number or other indicator within a range represented for example by the boundaries of 0 g and 2 g. That range may be divided into bands indicative of activity level, such that for example eight or ten different levels may be defined between an at-rest maternal condition at the lowest end of the range and a most vigorous activity condition at the upper end of the range.

In the case of a 1D accelerometer the single axis output may be used to determine an average activity value by again using the absolute difference between the current accelerometer sample and the previous sample point.

In this example, the processor 24 receives both the output of the maternal movement sensor 30 as well as the output(s) of the fetal movement sensor arrangement. The processor 24 can then compare the two inputs to determine whether or not an instance of fetal movement has occurred. In particular the output of the maternal movement sensor may be used to discount false positive readings of fetal movement recorded by the fetal movement sensor caused cue to maternal movement.

In one simple embodiment, the processor may simply discount any fetal movement readings recorded during periods of concurrent maternal movement above a certain threshold level. The processor may record the period of maternal movement so as to avoid distortion of the fetal movement count for a given time window. Thus average fetal movement values may be determined for a time period in which the mother is inactive either side (i.e. before and after) a period of activity. The average fetal movements/count may thus be applied by the processor for the period of activity in place of an actual count.

In a further embodiment, which is in many ways preferred, the level of maternal activity may be used to process/adjust the concurrent readings of fetal activity. For example the minimum threshold for recordal of an instance of fetal movement by the processor may be raised based upon a heightened level of maternal activity. The relationship between maternal and the threshold for recordal of fetal movement may be a linear or non-linear function (e.g. inversely exponential) or else may be determined according to one or more look up tables. Any such approach may be based on empirical findings. Additionally or alternatively, the recorded magnitude of fetal movement by the fetal movement sensor 16 may be reduced according to heightened maternal activity. The reduction may be inversely proportional or an exponential decay in line with the increase in maternal activity level or else some other function may be applied. Thus the required level of deflect required to be recorded by the fetal movement sensor may increase sharply with lower levels of activity but may tail of with higher maternal activity levels.

For example, when maternal activity is detected, e.g. corresponding to activity levels 2 to 3, the fetal movement signal may be attenuated by either a factor of six (for activity level 2) or by a factor of nine (for activity level 3).

The accelerometer or movement sensor 30 offers a substantial improvement in the accurate and reliable determination of a fetal movement by assisting in discrimination between fetal and maternal movements. The fetal movement sensor and accelerometer digitised data is processed by the processor 24 to detect and count the number of fetal movements. The processor may also provide a record of maternal activity based on the maternal sensor data as an additional output.

In one embodiment, the processor/controller 24 may be considered to comprise a fetal movement counter. The counter may be limited, for example by setting a maximum count threshold and/or time threshold (or else a maximum memory storage or else by limiting the power source) such that the monitoring device 13 can only be used for a single pregnancy.

Figure 3:
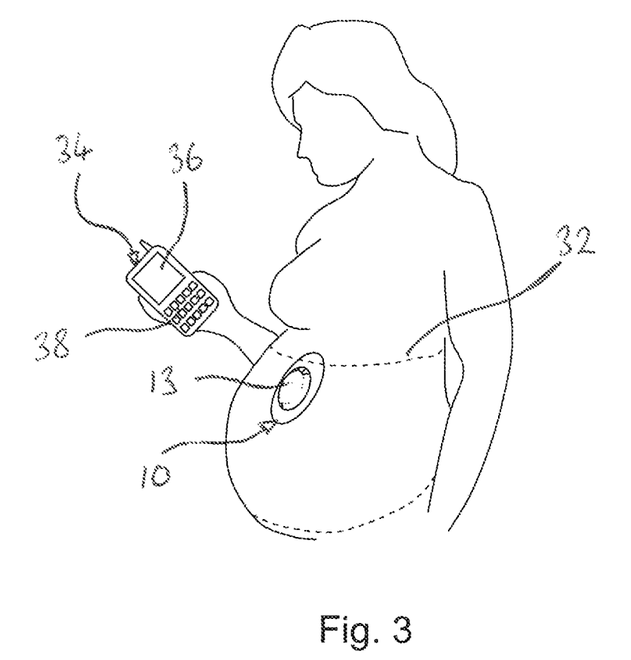
FIG. 3 shows examples of a system according to the present invention in use.

With reference to FIG. 3, there is shown the sensor device 10 in use, as worn by a mother. Since fetal movements tend to be experienced by a mother in one or more localised region of the abdomen, the sensor device 10 is placed on the abdomen in the region where the mother typically feels movement.

Whilst the deflection sensor device 10 described above is considered to provide an effective means for detecting fetal movement, it is to be noted that an alternative sensor arrangement 32 may be used additionally or alternatively.

The sensor arrangement 32 comprises a textile material arranged to be worn by the mother. The textile material is preferably in the form of a band which passes around the mother's abdomen. Ideally the textile material completely or substantially covers the abdomen and removes the need to place the sensor where the most fetal movements tend to occur. The textile material may thus be worn by the mother as part of or else beneath her usual apparel. Such a textile material may provide a distributed network of sensor elements.

The textile material comprises piezoelectric material in the form of filaments, fibres or one or more film strips. This material is either piezoelectric or piezoresistive and can be formed into wearable clothing, referred to as "intelligent textiles". Typically piezoelectric polymers may be used such as PVDF or co-polymers thereof. The textile material may comprise a fabric such as a knitted or woven fabric. In any form, the textile material may be formed in a manner such that it can stretch and thereby form a close fit over the mother's abdomen, such that the garment can experience stress/strain in response to deflections of the mother's abdomen caused by fetal movement. One such material is that supplied by FootFalls and Heartbeats Ltd in Wellington, New Zealand.

The piezoelectric component of the textile experiences a change in resistance when strain is applied to them in a manner similar to the deflection sensors 16 described above. For a piezo-resistive the change in electrical resistance due to the strain can be measured by applying a potential difference across the textile. For a piezoelectric material, the electric potential change in the material can be measured using the electronic means described above. Thus the textile sensor output may be similarly processed. For example, the output of the textile may be fed to an analogue front end amplifier and subsequently filtered and/or digitised to obtain suitable data for analysis by the processor 24.

Accordingly the textile sensor 32 may also comprise a housing 13 and the associated electronic components described above for processing, storing and/or transmitting the sensed deflections. The housing and associated electronics may be permanently fastened to the textile and/or removably attached thereto using attachment means as described above. That is to say the monitoring unit may be electrically and mechanically connected to the sensor.

One benefit of the textile sensor is that it may be used over an extended period of time, such that a single sensor garment 32 and associated housing 13 may be used for the duration of a pregnancy.

In either sensor embodiment, the processor may operate in a similar manner such that it can format and output the relevant data for transmission and/or process the data for output of the above-described log of fetal movement. The transmitter 28 can then transmit the output data via a wired or wireless data connection with a receiving device using conventional data transmission means and/or standards.

In embodiments of the invention a local receiving device is provided in the form of a portable communications device 34, which may comprise a mobile phone, smartphone, PDA, tablet, laptop or similar communication device having receiver/transmitter circuitry, a user interface and one or more processors. In the present embodiment, the device 34 comprises a user interface in the form of a touch-screen 36 and/or one or more keys 38.

The monitoring device on the mother's abdomen transmits the processed data via a radio signal (e.g. Wi-Fi, Bluetooth®, Bluetooth Low Energy or suitable standard, such as a mobile telephony standard) to the device 34. The link between the monitor device and the receiving device 34 can also be wired (e.g. for retrospective download, for example via a USB link, to any of the above described devices or a personal computer). In a preferred embodiment a Bluetooth® link is used such that the monitor device and the device 34 can be paired and can subsequently transmit/receive as required.

The receiving device 34 can thus log and analyse the received data, for example in order to undertake the above-described processing or further processing thereof.

In examples of the present invention, the user/receiving device 34 comprises a further sensor in the form of a tactile sensor or user input sensor or interface. The device 34 comprises a processor under the control of one or more modules of machine readable code. The machine-readable instructions or code may be provided in the form of one or more software application running on the device. The code may be stored on the device and/or provided using any conventional data carrier including download over a suitable network connection.

Using the device 34, the mother may record or log perceived fetal movements as they are felt. With the software application running, the mother may depress a key 38 or touch the screen 36 to log a record of fetal movement at the time it is felt. The record of fetal movement may then be stored in the device memory along with the time at which it occurred. In some embodiments the mother may be able to enter a perceived strength of the fetal movement, for example by depressing a key or touching the screen for a length of time indicative of the perceived strength of movement, or else by pressing the user interface a number of times in quick succession.

The software application may provide one or more further functions, such as allowing the mother or other user to review, amend and/or delete entries.

The processor in the device 34 is arranged to receive the record of perceived fetal movement by the mother and compare it to the concurrent log of fetal movement data received from the sensor device such that the processor can compare and or analyse those two inputs. In one embodiment, the communication device 34 and sensor device 10 may undergo a time synchronisation routine so as to ensure the timer 26 and a timer within the device 34 correspond, for example to the nearest second. This may be achieved using a simple routine over a Bluetooth® connection wherein the clock of one device is updated to match the instantaneous time on the clock of the other device.

The device 34 processor may process both the received fetal movement records/data in order to determine a final (e.g. verified) fetal movement log. For example the processor may compare the times of the sensed and perceived records of instances of fetal movement and may determine an actual instance of fetal movement if the sensed and perceived records were recorded at the same time or else within a predetermined time threshold, e.g. within a threshold of between 1 and 10 seconds.

In other embodiments, the user interface device described above may be swapped for, or supplemented with, a different user interface device. Such as user interface device may be used to log fetal movements perceived by other means. For example a carer may perceive fetal movements by touching a mother's abdomen or else by using another device capable of sensing or allowing a user to perceive fetal movements. Such a device could comprise a microphone/speaker, Doppler or other ultrasound device or other conventional equipment. Such a device may also comprise a personal computer or other conventional computing means connected to suitable sensing equipment and programmed accordingly. A user of such equipment may manually input a log of fetal movement or else the equipment itself may be calibrated to automatically detect movements.

In the event of a record of sensed or perceived fetal movement for which there is no corresponding entry within the other record, the processor may determine that either the sensed or perceived record takes precedent. Additionally a weak (e.g. lower magnitude) sensed input may be verified by the presence of a corresponding perceived input.

By comparing the sensed and perceived fetal movement records, the processor may determine one or more characteristic of the sensed records which are indicative of a positive or negative fetal movement. For example, the processor may determine a threshold sensed magnitude of deflection (e.g. and/or direction or duration or timing) which is indicative of a confirmed fetal movement by the mother. In this way the processor may dynamically adjust a threshold parameter value or criterion for determination of a fetal movement from the sensed readings.

In one embodiment the processor may have one or more initial threshold criterion. The processor or system may have a normal mode of operation, in which the processor receives only the sensed output of fetal movement from sensor device 10, wherein the one or more threshold criterion is fixed. The processor or system may have a further mode of operation in which the processor receives both the sensed output of fetal movement from sensor device 10 and also the concurrent input of perceived fetal movements from the mother, or other means, wherein the one or more threshold criterion is variable or can be altered by the processor.

In addition to, or else instead of, modifying the criteria for determining a fetal movement, the processor may log all sensed fetal movements but may apply a confidence value to each record based on the comparison of, or correlation between, the sensed and perceived fetal movement records.

The further mode of operation may be considered to comprise a learning or calibration mode. Such a mode of operation can improve the reliability of the results and/or tailor the operation of the system to a particular mother. The application software on the device may prompt the mother or other user to input perceived fetal movements, thereby initiating the learning mode of operation. For example the mother may be prompted to log perceived fetal movement for a set period of time (e.g. such as one or two hours) upon first use of the system and/or at one or more intervals thereafter. Regardless of whether a learning mode is initiated by the device, a mother or other user may access the application software on the device 34 at any time to register a log of perceived fetal movement, the processor may initiate the learning mode upon determining that both fetal movement logs are available for a concurrent time period.

Thus the mother or a carer may establish a routine, such as a daily or weekly routine, wherein a log of perceived fetal movement is input on a regular basis. Accordingly the mother may choose a suitable time of day when she can rest, whilst provide the required input. Additionally or alternatively, the processor may control the output of a prompt or alarm via the device to inform the mother to input a log of fetal movement, for example by way of on-screen instructions or an audible message. This may be triggered for example at routine intervals or else by a determination of abnormal fetal movement by the processor based on the sensed fetal movement records.

In one example, the learning mode may be supervised in a medical facility, for example with the assistance of a carer. There may be an output indicative of the success of the learning mode, for example by way of the confidence value, such that the mother can use the device thereafter at home.

Figure 6A:
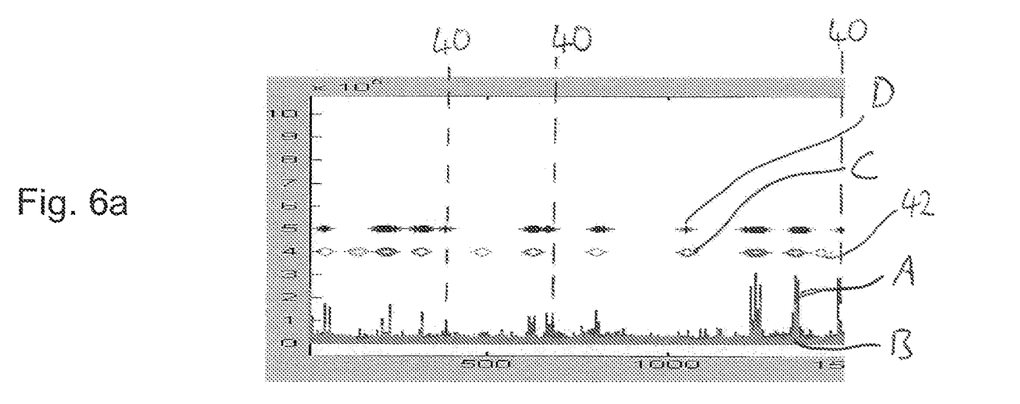
FIGS. 6a and 6b show example plots of results obtained using a sensor arrangement according to the invention.
Figure 6B:
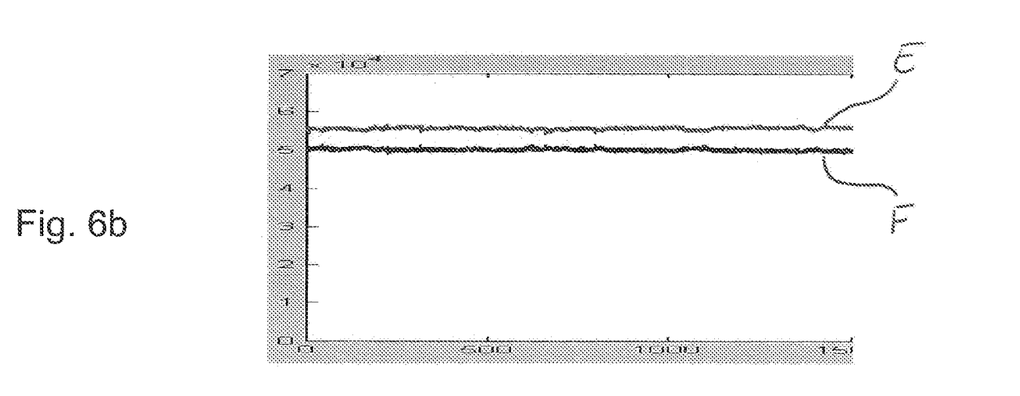

The processor maintains a log of fetal movement or 'kick count' over time, for example such that a visual display in the form of a plot of fetal movement can be generated for reporting purposes. The plot may provide a useful medical record for use/review by the clinician or midwife in determining the wellbeing of the fetus and/or mother. The processor may also log one or more of the associated parameters described above along with, or in addition to, the fetal movement record. Examples of such records are shown in FIGS. 6-8.

A clinical trial involving the monitoring of deflections in a pregnant mother's abdomen was performed using the sensor device 10 described above and the results were compared with the results of fetal movement generated using an ultrasound imaging transducer. An example of the typical output of this trial is shown in FIG. 6, in which the x-axis represents time in seconds and the y-axis represents the following parameters:
A. First fetal sensor signal filtered and rectified (e.g. using absolute value)
B. Second fetal sensor signal filtered and rectified (e.g. by absolute value)
C. Perceived fetal movement event (input by mother) on device 34
D. Observed fetal (limb or trunk) movement record from ultrasound imager
E. Upper trace—x deflection recorded by accelerometer
F. Lower trace—z deflection recorded by accelerometer These traces show a clear correlation between the ultrasound imager detected fetal movements (D) and maternal perceived movements (C). It is noted that the correlation is not 100% but is of the order of approximately 85-90% since some fetal movements were either missed or they were too small to be discernible by the mother. The piezoelectric sensors also show good correlation with the ultrasound imager, especially for the first sensor A. It is important to note that there are some instances of fetal movement, for example occurring at dashed lines 40, for which there was no perceived movement recorded by the mother but there was a sensed fetal movement by the sensors. Furthermore there are instance indicated at 42, for which the mother erroneously recorded a fetal movement but where there was no movement observed using ultrasound imaging. Accordingly, sensor arrangement does have the ability to provide more accurate and consistent results than relying on the mother's perception of fetal movement alone. Furthermore the results show that the use of a mode of operation in which both the mother's perceived movements and also the sensor output has the capability to further improve the accuracy of fetal movement detection.

Figure 7A:
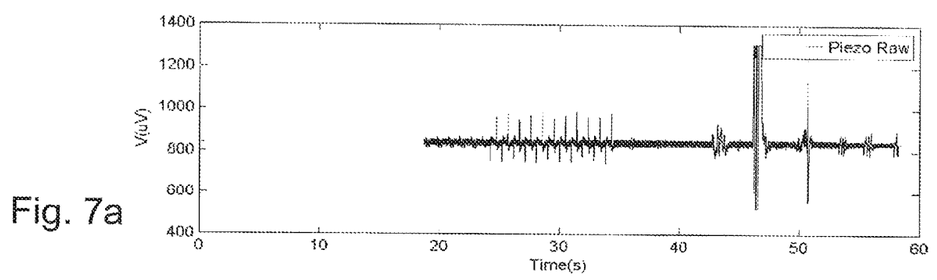
FIGS. 7a and 7b show the output of two different examples of fetal movement sensor for use in conjunction with the present invention.
Figure 7B:
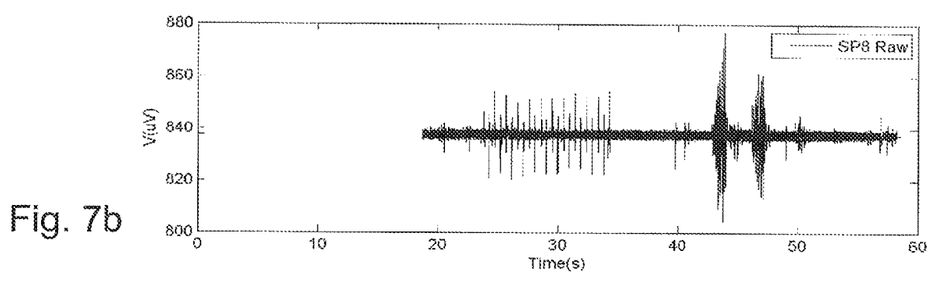

In FIG. 7 there are shown comparative traces of sensor output for the piezoelectric sensor 16 (FIG. 7a) against a corresponding output using the piezo-resistive intelligent textile 32 in response to a series of different types of input deflection force. Here it can be seen that there is a very good correlation between the determinations of a deflection event but that each type of sensor responds more effectively to different types of deflections. Accordingly it is envisaged that further tailoring of the sensor device may lean towards one or the other sensor type or a combination thereof in order to best suit the intended use.

Figure 8:
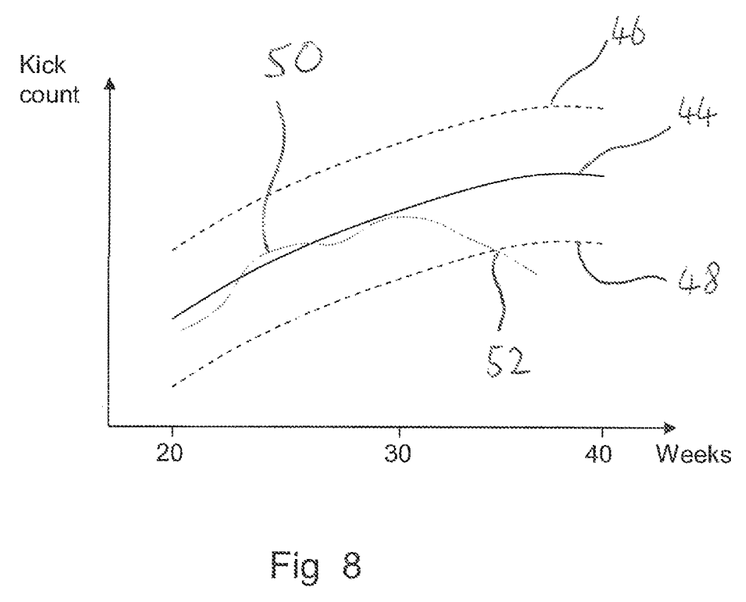
FIG. 8 shows an exemplary plot of fetal movement over a gestational period.

In FIG. 8, there is shown a schematic plot of fetal movement count over an extended period of use, including a number of days or weeks. There is significant diurnal variation in normal fetal activity which changes gradually with gestation. Accordingly line 44, represents a mean or average fetal movement count over a gestational period. A region or normal fetal movement may be identified as the area between upper 46 and lower 48 boundaries or thresholds either side of the mean line 44. The upper and lower boundaries may be determined based on percentiles or other correlations, such as fetal activity levels associated with, or generally indicative of, fetal abnormalities or increased risks of adverse development or well-being.

An example of a plot of fetal activity obtained using one of the above described embodiments is shown at 50. Here it can be seen that where the plot 50 crosses the lower boundary 48, the processor determines that abnormal or reduced fetal movements have occurred indicative of an undesirable fetal condition. Such a determination may additionally or alternatively be made based on the gradient of the plot 50 or else a relative change in the fetal movement count (for example by way of a reduction in fetal movement of 10% or more).

Upon making a determination of undesirable levels or trends in fetal activity, the processor may control the output of one or more alarms and/or instructions to the mother. The processor may be programmed to determine different levels of risk associated with different fetal activity levels or changes in fetal activity.

The processor may control output of an alarm or other visual, audible or tactile alert to the mother warning her of reduced fetal movement. The alert may for example advise the mother to contact a medical professional. In one embodiment, for example indicative of a relatively low level of risk, the device may output an on-screen instruction or message for the mother to reposition the sensing device and/or commence recording of perceived fetal movements. This may allow verification of the finding of reduced fetal movement or else may allow the device to enter a learning/recalibration mode, following which the device may enter a normal mode of operation if the sensed/perceived fetal movement count returns to an acceptable level.

Figure 5:
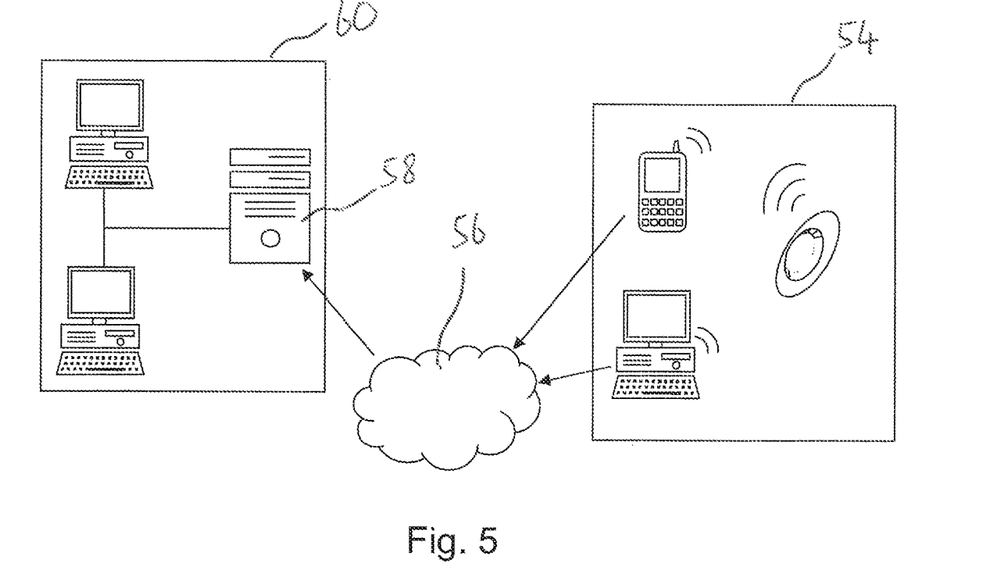
FIG. 5 shows a communication system according to a further example of the invention.

Turning to FIG. 5, there is shown a system by which the invention may be used to provide a medical record for use at a medical facility or else by a medical professional. The sensor device 10 and device 34 as described above may be used by a mother, for example in a home environment 54. The device 34 is arranged to transmit the amassed fetal movement records (i.e. the count of fetal movements over time) via a suitable network 56 (i.e. a wide area network such as the internet and/or a mobile telephony network) to a server 58 for a medical facility 60 (i.e. at a designated IP address). Additionally or alternatively the device may send only an alert signal to the medical facility upon determination of reduced/undesirable fetal movement. One or more networked computing devices at the medical facility may receive the relevant data for review. The signal sent from the device 34 typically comprises an identifier of the mother such that the medical facility can contact the mother to arrange an assessment.

The mother may manually transmit the full fetal movement records or may take the device 34 with her or another memory device with the records stored thereon for access at the medical facility. The fetal movement records may then be stored by the medical facility for analysis in relation to the medical history of the mother.

Accordingly the sensing/monitoring equipment described above may provide an additional source of information for the assessment of the wellbeing of the mother and/or fetus. The sensing equipment (and/or device 34) may be provided by the medical facility as part of a home monitoring program for the mother. For example, in an instance in which there is reason for concern over the wellbeing of a mother and/or fetus, the mother can be asked to use the device for prolonged periods of time such that, if any instances of reduced fetal movement are detected, the mother can attend a medical facility for further assessment. This provides an additional level of assurance between continual assessment within a medical facility and relying solely on a mother's self-assessment of reduced fetal movement in a home environment. Accordingly the invention can help to reduce false diagnoses of reduced fetal movement and/or increase accurate determinations thereof. As well as increasing the level of care available to pregnant mothers, the invention can thus help to reduce burden on antenatal facilities and/or personnel in hospitals or other medical facilities.

The fetal movement device is therefore designed to detect and count perceived fetal movements either automatically or semi-automatically. The intention is that the device is placed on the abdomen of a pregnant subject daily for prolonged periods of time from 20 weeks gestation until 40 weeks gestation/delivery. Thus the device can provide continuous monitoring of long term trends of fetal movement.

In one mode of use, the sensing device can be applied/worn on the mother's abdomen at night so as to record fetal movement at a time when the mother is naturally at rest. As well as helping to avoid the interference caused by maternal movements, the use of the device in this manner may provide an additional (otherwise untapped) source of information to the self-assessment of fetal movements by the mother during the daytime.

Whilst certain embodiments of fetal movement sensors are described in detail above, it is to be noted that a variety of other sensing devices may find application in the context of the invention, e.g. other than piezo devices, such as strain gages, microphones or surface electrodes. Any or any combination of such sensors may be used in isolation or in conjunction with the maternal movement sensor described above.

The receiving device 34 may be implemented as bespoke remote device hardware or else using a general purpose device having bespoke machine readable instructions thereon. Given the user interface and/or data processing/storage/transmission requirements of the remote device as described above, it will be appreciated that general purpose devices, such as mobile phones, PDA's, laptops, tablet computers, programmable media players or the like may provide useful, readily-available hardware for implementing the user interface aspect of the invention. However in other embodiments a bespoke user interface device may be provided which may be more readily accessible to a mother, in the form of for example a wrist strap, neck strap, an arm or waist band, or else a clip device for attachment to clothes or the like. Such embodiments may prove beneficial for ongoing monitoring of a mother's perceived sensations of fetal movement in the event that the time of recordal of a perceived fetal movement may be required to correlate to the timing of a reading by the fetal movement sensor on the mother's abdomen.

Furthermore in other embodiments, the tactile input/learning mode could be implemented using a switch, push button or other tactile sensor mounted on the sensor device itself. This may negate the need for a further user input or communication device, albeit by increasing the cost and complexity of the device to be worn by the mother.

It is also to be noted that the addition of other sensors to the sensing device could allow further care/monitoring of the pregnant mother. Such additional sensors could comprise:

Fetal heart rate, maternal heart rate, maternal uterine activity, maternal temperature maternal blood pressure, maternal respiration rate. These parameter can be obtained by the current sensors or extra sensor such as surface electrodes, pressure sensor, thermometer, etc Record fetal heart rate alongside fetal movements to provide HRV (Heart Rate Variability) analysis or beat to beat analysis as part of a Non Stress Test—a test routinely implemented by the clinical care team.

In such embodiments, an instance of recording one or more further maternal or fetal vital signs could be initiated upon determination of reduced or abnormal fetal movement. Additionally or alternatively, those further sensor signals could be recorded in conjunction with the fetal movement count to provide a more detailed report of fetal/maternal wellbeing.

In any embodiment, the recorder electronics described above could be embedded into a single integrated circuit, so as to provide a miniaturised recorder which can thus be embedded conveniently in a suitably portable monitoring device.

The invention claimed is:

1. A fetal movement monitoring apparatus comprising:
  a first sensor device comprising a piezoelectric or piezoresistive sensor component configured to be applied to a mother's abdomen for detection of fetal movements, wherein the first sensor device is configured to output a signal comprising one or more record of said fetal movements;
  a second sensor device in a receiving device to detect user input comprising a record of perceived fetal movements; and
  one or more processor under the control of machine readable instructions configured to:
    detect that the fetal movement monitoring apparatus comprises a mode of operation that is based at least in part on a combination of the signal from the first sensor device and the user input detected by the second sensor device, wherein the first sensor device and the second sensor device are both included as part of the fetal movement monitoring apparatus;
    compare the signal of the first sensor device and the user input detected by the second sensor device;
    determine a confidence value associated with said comparison;
    calibrate the first sensor device based upon said comparison; and
    process the signal from the first sensor device to output a log of the fetal movements during a period of time and the confidence value.

2. The fetal movement monitoring apparatus according to claim 1, wherein the first sensor device comprises a deflection sensor arranged to sense deflections in the mother's abdomen indicative of a fetal movement.

3. The fetal movement monitoring apparatus according to claim 1 wherein the first sensor device comprises a plurality of fetal movement sensors arranged at spaced locations and/or different relative orientations.

4. The fetal movement monitoring apparatus according to claim 1 wherein the first sensor device comprises a patch comprising an adhesive material for adhering the patch to the mother's abdomen.

5. The fetal movement monitoring apparatus according to claim 1, wherein the first sensor device comprises an intelligent textile material to be worn by the mother in the abdominal region, the stress/strain in said textile material being sensed to provide an indication of fetal movement.

6. The fetal movement monitoring apparatus according to claim 1, wherein the second sensor device comprises a tactile sensor and a timer or clock, which may be synchronised with a corresponding timer or clock in the first sensor device.

7. The fetal movement monitoring apparatus according to claim 6, wherein the second sensor device comprises a user interface device, separate from the first sensor device and arranged for data communication therewith, the user interface device having one or more processors for processing of the sensor signals.

8. The fetal movement monitoring apparatus according to claim 7, wherein the user interface device has a display and the one or more processors control output of prompts to the user to commence input of perceived maternal movements using the device.

9. The fetal movement monitoring apparatus according to claim 1, wherein the first sensor device comprises any, or any combination, of an amplifier, bandpass filter, analogue-to-digital converter and/or data sampler.

10. The fetal movement monitoring apparatus according to claim 1, comprising a further sensor in the form of a maternal movement sensor, the further sensor being different to the first or second sensor and being arranged to sense coarse maternal movement.

11. The fetal movement monitoring apparatus according to claim 10, wherein the maternal movement sensor is arranged to be applied to the mother's skin, or worn by the mother, as part of the first sensor device.

12. The fetal movement monitoring apparatus according to claim 10, wherein the maternal movement sensor comprises an accelerometer.

13. The fetal movement monitoring apparatus according to claim 10, wherein the one or more processor is arranged to compare a signal output from the maternal movement sensor with the signal output from the first sensor device and to output the log of fetal movements over time based upon said comparison.

14. The fetal movement monitoring apparatus according to claim 13, wherein the processor is arranged to process the signal output from the first sensor device and to accept or record or reject an instance of fetal movement in dependence upon a concurrent sensed level of maternal activity.

15. The fetal movement monitoring apparatus according to claim 1, wherein the comparison performed by the processor comprises comparing the time and/or magnitude of any records or signals.

16. The fetal movement monitoring apparatus according to claim 1, wherein the log of fetal movements comprises a summation or count of fetal movements over a predetermined time period.

17. The fetal movement monitoring apparatus according to claim 1, wherein the processor compares the log of fetal movements to one or more predetermined threshold value, such as a predetermined count or rate of fetal movement and/or a predetermined rate of change of fetal movement and outputs a signal indicative of abnormal fetal movement if the log of fetal movement meets or passes said one or more predetermined threshold value.

18. The fetal movement monitoring apparatus according to claim 17, wherein the threshold value is a variable which varies according to a predetermined trend and/or in response to previous logs of fetal movement.

19. The fetal movement monitoring apparatus according to claim 1, wherein the processor is configured to compare the output of the first sensor device and the user input detected by the second sensor device in response to an indication of abnormal fetal activity.

20. The fetal movement monitoring apparatus according to claim 1, further comprising a transmitter for transmitting the log of fetal activity or an alert signal derived therefrom to a remote location.

21. A method of monitoring fetal movement comprising:
obtaining or receiving a signal comprising a first record of fetal movements from a first sensor device applied to a mother's abdomen;
obtaining or receiving a second record of perceived fetal movements manually input by a user for a time period concurrent with the first record of fetal movement; and
using one or more processor under the control of machine readable instructions to:
compare the signal of the first sensor device and the user input;
determine a confidence value associated with said comparison;
calibrate the first sensor device based upon said comparison; and
process the signal from the first sensor device to output a log of the fetal movements during a period of time and the confidence value.

22. The method according to claim 21, wherein the user is the mother.

23. A data carrier comprising machine readable instructions for the control of one or more processors to:
receive a signal comprising a first record of fetal movements from a first sensor device applied to a mother's abdomen;
receive a second record of perceived fetal movements manually input by a user for a time period concurrent with the first record of fetal movement;
compare the signal of the first sensor device and the user input;
determine a confidence value associated with said comparison;
calibrate the first sensor device based upon said comparison; and
process the signal from the first sensor device to output a log of the fetal movements during a period of time and the confidence value.

* * * * *